United States Patent
Garcia et al.

[11] Patent Number: 5,907,110
[45] Date of Patent: May 25, 1999

[54] FLUID SAMPLING TOOL

[75] Inventors: Anthony R. Garcia, Espanola; Roger G. Johnston, Los Alamos; Ronald K. Martinez, Santa Cruz, all of N.M.

[73] Assignee: The Regents of the University of California, Los Alamos, N.M.

[21] Appl. No.: 09/087,118

[22] Filed: May 29, 1998

[51] Int. Cl.⁶ .............................. G01N 1/10; G01N 1/04
[52] U.S. Cl. .................... 73/864.74; 73/864.73; 73/864.43; 73/863.85
[58] Field of Search ............ 73/863.85, 864.51, 73/864.52, 864.73, 864.74, 863.86

[56] References Cited

U.S. PATENT DOCUMENTS

| | | | |
|---|---|---|---|
| 4,350,052 | 9/1982 | Kendall | 73/863 |
| 5,558,140 | 9/1996 | Clark, II | 141/98 |
| 5,704,383 | 1/1998 | Kammeraad | 137/15 |

*Primary Examiner*—Hezron Williams
*Assistant Examiner*—Chad Soliz
*Attorney, Agent, or Firm*—Samuel L. Borkowsky

[57] ABSTRACT

A fluid sampling tool for sampling fluid from a container. The tool has a fluid collecting portion which is drilled into the container wall, thereby affixing it to the wall. The tool may have a fluid extracting section which withdraws fluid collected by the fluid collecting section. The fluid collecting section has a fluted shank with an end configured to drill a hole into a container wall. The shank has a threaded portion for tapping the borehole. The shank is threadably engaged to a cylindrical housing having an inner axial passageway sealed at one end by a septum. A flexible member having a cylindrical portion and a bulbous portion is provided. The housing can be slid into an inner axial passageway in the cylindrical portion and sealed to the flexible member. The bulbous portion has an outer lip defining an opening. The housing is clamped into the chuck of a drill, the lip of the bulbous section is pressed against a container wall until the shank touches the wall, and the user operates the drill. Wall shavings (kerf) are confined in a chamber formed in the bulbous section as it folds when the shank advances inside the container. After sufficient advancement of the shank, an o-ring makes a seal with the container wall.

14 Claims, 6 Drawing Sheets

FLUID SAMPLING TOOL

FIELD OF THE INVENTION

The present invention relates generally to chemical sampling tools and, more particularly, to tools that allow the withdrawal of a fluid sample from a sealed container without spillage. This invention was made with government support under Contract No. W-7405-ENG-36 awarded by the U.S. Department of Energy to The Regents of the University of California. The U.S. Government has certain rights in the invention.

BACKGROUND OF THE INVENTION

The treatment and disposal of stored hazardous waste is a challenge. It is often necessary to store waste in a container since, at present, there may be no effective procedure for treating it. It also may be that the waste is not sufficiently characterized to make a determination of the appropriate treatment procedure. Thus, large quantities of untreated waste remain stored in containers and are awaiting treatment.

A typical waste storage container for a liquid waste is a metal drum. Waste is poured into the container, and a lid is sealed to the container to prevent the waste from escaping. Since an analysis of the waste composition from a sealed container may be necessary before an appropriate treatment and disposal procedure is implemented, a device for extracting a sample of waste from a sealed container is required.

Similar devices would be useful for extracting samples from munitions that may contain dangerous chemicals. Importantly, during a sampling procedure, the user must avoid exposure to the material being sampled while obtaining a sample, and while transporting the sample to a site for analysis. Devices that allow one to sample the fluid contents of sealed containers are known.

In U.S. Pat. No. 4,350,052 entitled "Apparatus and Method for Tapping and Extracting Oil Samples From an Underground High Pressure Pipe-Type Transmission Cable System" by R. W. Kendall, which issued Sept. 21, 1982, an apparatus and method for extracting oil from a high-voltage cable is described. After removing any covering from the outer surface of the cable, the nipple of the apparatus is welded to the cable, forming a chamber. After a hole is drilled in the cable and the drill bit is withdrawn, the chamber fills with oil from the cable. A ball valve is installed to control the flow of oil out of the cable.

In U.S. Pat. No. 5,704,383 by D. A. Kammeraad et al. entitled "Tool and Method for Removing Fluid From Container", which issued Jan. 6, 1998, a tool for tapping and removing fluid from a container is described. A frustoconically-shaped shank having a threaded outer surface sealingly engages the container wall as the shank is advanced into the container. Opposing inlets in the bit communicate with an internal passageway within the shank to allow fluid from the container to enter the tool. The tool is provided with a sealing surface that deforms the container wall while providing a seal between the sealing surface and the wall. Advancement of the frustoconically-shaped shank into the container wall increases the borehole size. An assembly attached to the shank houses a piston that serves as a valve for preventing fluid in the shank passageway from escaping to the outside. A fluid collection unit can be attached to the valve assembly to obtain fluid samples.

In U.S. Pat. No. 5,558,140 by J. E. Clark II entitled "Device For Draining Fluid From a Container", which issued Sept. 24, 1996, a fluid draining device for removing oil is described. The device has a threaded screw with a sharpened puncturing tip and an internal fluid channel with at least one opening just behind the tip. It also has a threaded screw guide connected to a strap which can be wrapped around a container and tightened. An opening in the strap coaxial with the bore of the screw guide allows the screw to pass through the strap. An optional sealing material placed in between the strap and the container wall may be used to provide a seal with the wall.

A portable tool for rapidly sampling fluid from a sealed container while preventing exposure to the contents is clearly desirable.

Therefore, an object of the invention is to provide a portable fluid sampling tool for collecting fluid from a sealed container without exposing the user or the environment to the fluid.

Another object of the invention is to provide a fluid sampling tool that can be drilled into a sealed container without exposing the user to wall shavings created during drilling.

A further object of the invention is to provide a fluid sampling tool from which a fluid sample or multiple fluid samples can be easily and rapidly withdrawn from sealed containers.

Yet another object of the invention is to provide a fluid sampling tool where plumbing may be rapidly attached to enable fluid sampling from a container.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the objects and purposes of the present invention as embodied and broadly described herein, the present invention includes a rotatable tool for collecting and sampling fluid through a container wall, comprising a drilling member having a fluted shank with a cylindrical threaded tapping section and a drilling end portion for drilling a hole into the wall of the container, whereby kerf is generated. The tool has a cylindrical housing member having an inner axial passageway therethrough, the passageway widening near one end to provide an annular flat surface perpendicular to the housing member axis and having a threaded inner surface, the other end of the housing member having a threaded inner surface for receiving the threaded shank of the fluted drilling member. The tool also has a septum which fits into the widened threaded passageway of the housing member to provide a leakproof seal with the annular surface, and a cylindrical threaded insert having an inner axial passageway therethrough, the insert being capable of threaded engagement with the widened threaded passageway in the housing and being capable of compressing the septum against the annular surface to provide a leakproof seal with the annular surface. The tool also has a flexible member adapted to form a seal with the housing member, the flexible member also capable of forming a chamber to capture and enclose kerf generated, the flexible member also being capable of forming a seal with a container wall. The present invention may also include a retaining ring attached to the housing in between the first end portion and the second end portion of the housing for preventing the flexible member from sliding along the housing member. The present invention may also include a piercing sampling means for withdrawing fluid from the passageway in the housing.

BRIEF DESCRIPTION OF THE DRAWINGS

The accompanying drawings, which are incorporated in and form a part of the specification, illustrate embodiments of the present invention and, together with the description, serve to explain the principles of the invention.

In the Figures.

DETAILED DESCRIPTION OF THE INVENTION

The present fluid sampling tool invention combines a fluid collecting section and a fluid extracting section for obtaining fluid samples from a sealed container. Reference will now be made in detail to the present preferred embodiments of the invention, examples of which are illustrated in the accompanying drawings. Similar or identical structure is identified using identical callouts.

Figure 1:
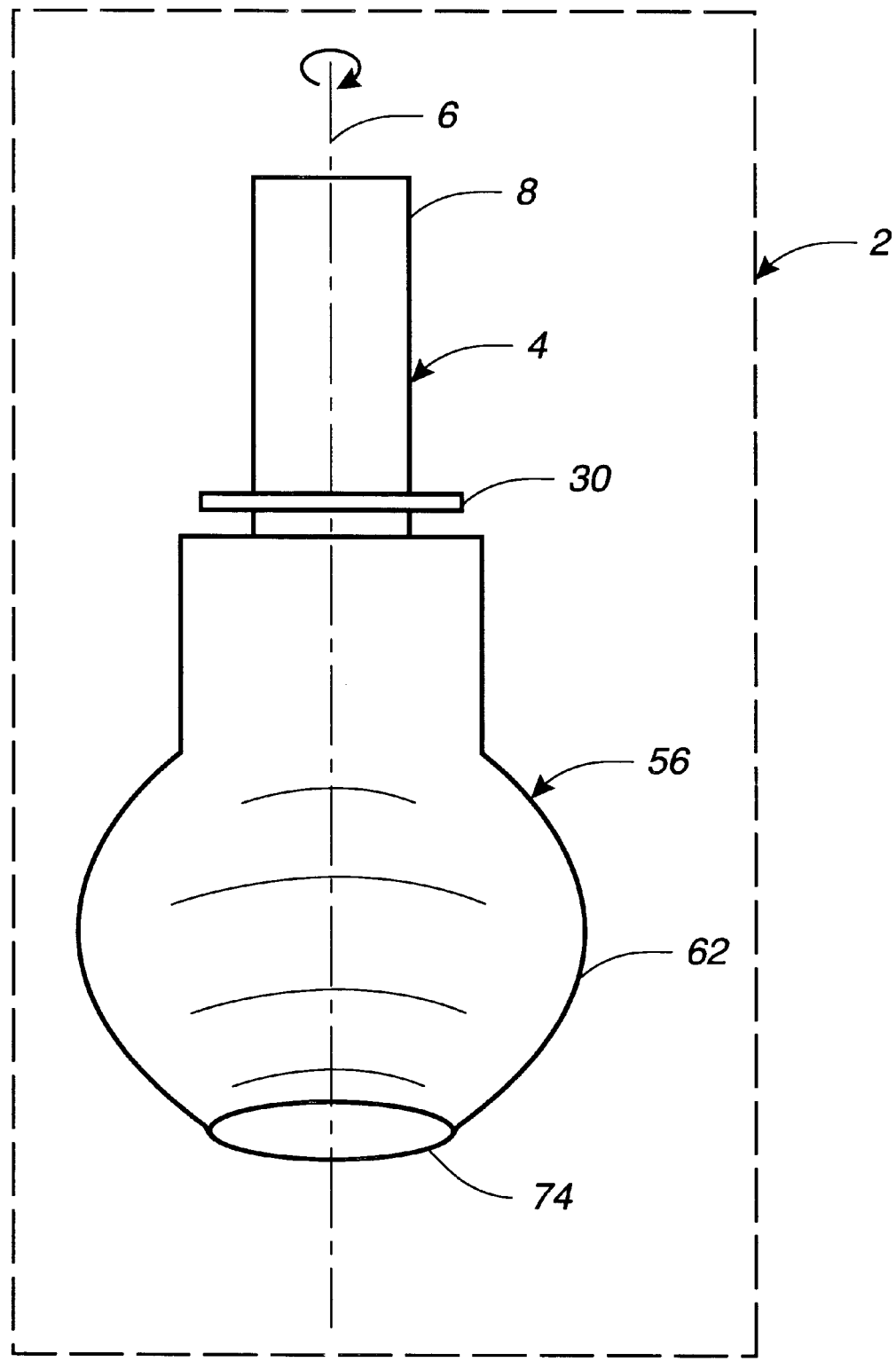
FIG. 1 shows a perspective side view of the fluid collecting section of the present fluid sampling tool.

Turning now to the figures, FIG. 1 shows a perspective side view of the fluid collecting section 2 of the present fluid sampling tool ready for affixing to a container wall. FIG. 1 shows housing 4 having an axis 6 and a first housing portion 8 which may be clamped into the chuck of a power drill (not shown) and caused to rotate about axis 6. FIG. 1 also shows a retaining ring 30 for preventing flexible member 56 from sliding along housing 4 toward first housing portion 8 while fluid collecting section 2 is being affixed to a container wall.

Figure 2:
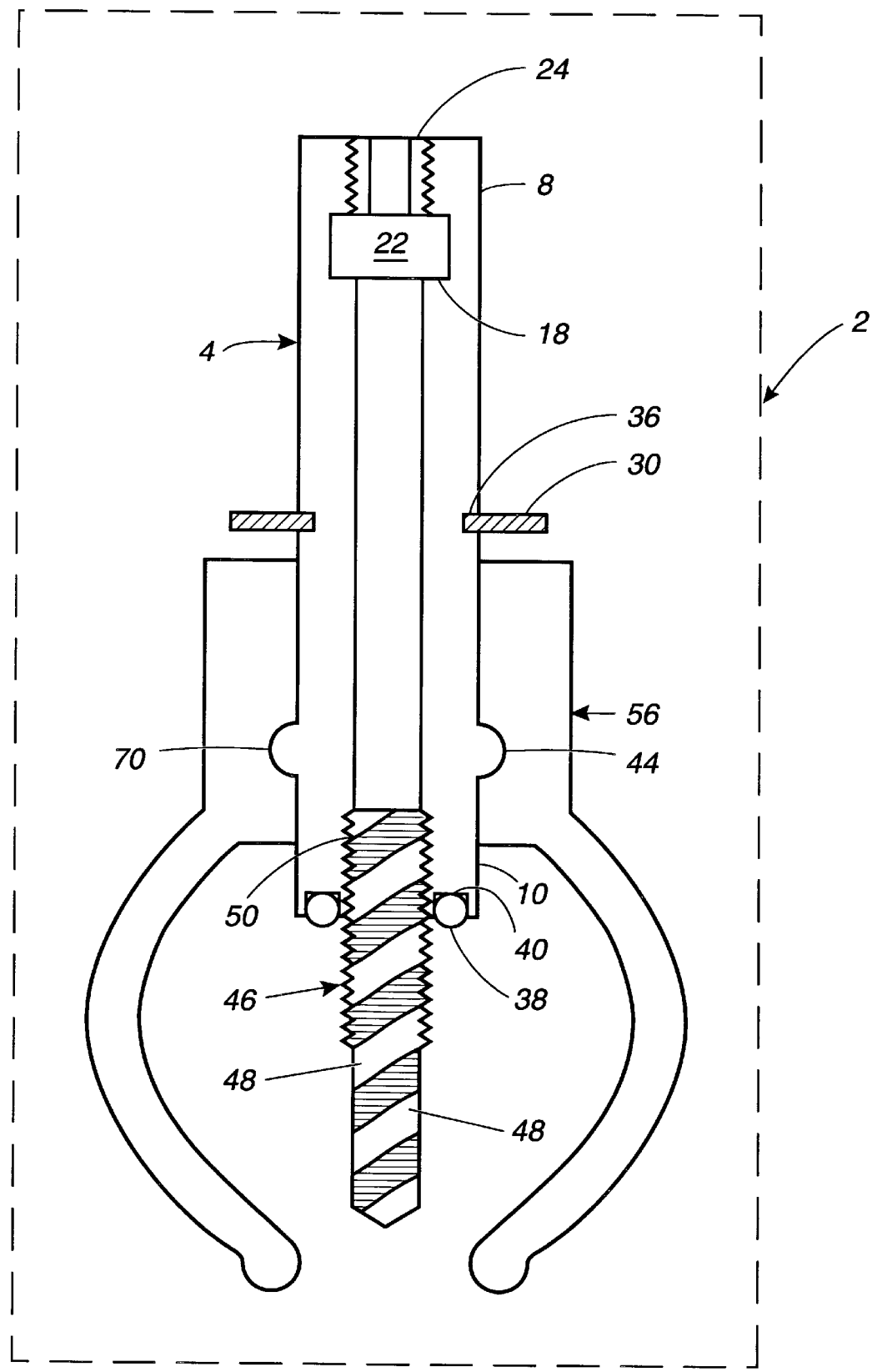
FIG. 2 shows a cross-sectional side view of the fluid collecting section of FIG. 1.

FIG. 2 shows a cross-sectional side view of fluid collecting section 2, showing fluid collecting section 2 having septum 22 sealingly compressed against first end portion 8 of housing 4 by a hollow threaded insert 24. Fluid collecting section 2 also has an o-ring 38 which fits into an annular groove 40 in second end portion 10 of housing 4. Flexible member 56 is compressed against housing 4 and positioned such that inner groove 70 of flexible member 56 receives circumferential protrusion 44 of housing 4. FIG. 2 also shows a shank 46 having flutes 48, and a first end 50 threadably engaged within second end portion 10 of housing 4.

Figure 3:
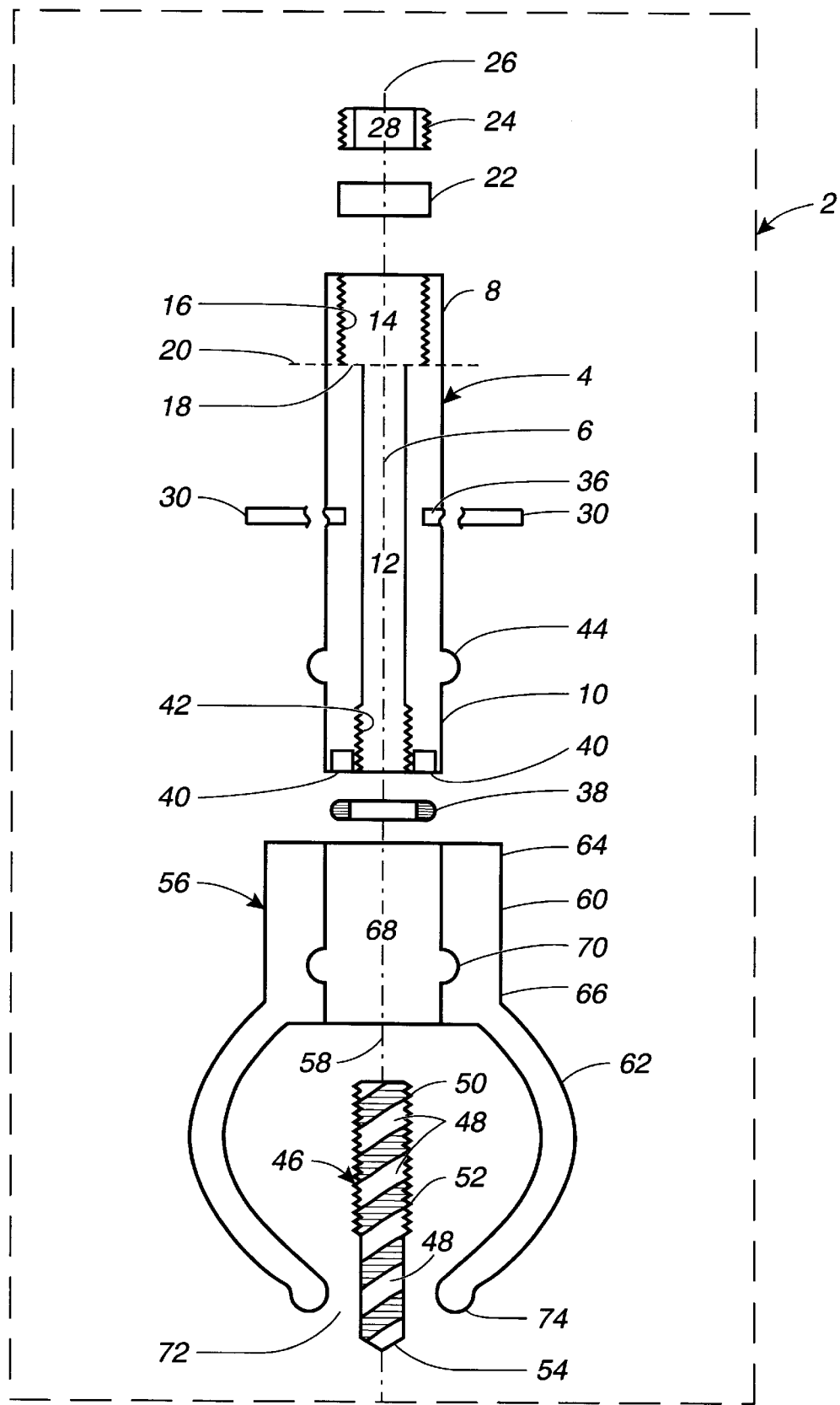
FIG. 3 shows an exploded cross-sectional side view of the fluid collecting section of FIG. 2.

FIG. 3 shows an exploded cross-sectional side view of fluid collecting section 2, including cylindrical housing 4 having an axis 6, a first end portion 8, a second end portion 10, and an inner axial passageway 12 therethrough. A widened passageway section 14 is formed in passageway 12 in first end portion 8 of housing 4, and is defined by first inner threaded housing surface 16 and inner annular flat surface 18 having a surface plane 20 perpendicular to axis 6 of housing 4. FIG. 3 also shows fluid collecting section 2 having pierceable septum 22 adapted to fit inside widened passageway section 14 and seal against annular surface 18. Fluid collecting section 2 also includes hollow threaded insert 24 having an axis 26 and an inner axial passageway 28 therethrough. Retaining ring 30 is adapted to be received by circumferential groove 36 in housing 4. O-ring 38 fits into annular groove 40 located in the end of second end portion 10. Second inner threaded housing surface 42 defines passageway 12 in the vicinity of second end portion 10 of housing 4. Housing 4 also includes a lateral circumferential surface protrusion 44 located at second end portion 10.

Single piece cylindrical shank 46 includes flutes 48, a first shank end 50 having an outer threaded surface 52 capable of threaded engagement within second end portion 10 of housing 4, and a sharpened second shank end 54 configured to drill a hole into the wall of a container. For sufficiently thick walls, outer threaded surface 52 is capable of tapping the hole drilled by shank 46 as shank 46 advances into the wall.

Fluid collecting section 2 also includes flexible member 56 having an axis 58, a cylindrical portion 60 and a hollow bulbous portion 62. Cylindrical portion 60 has a first end 64 and a second end 66 and an inner axial passageway 68 therethrough. Passageway 68 has a diameter narrower than the outer diameter of housing 4 so that when second end portion 10 of housing 4 is slid through first end 64 of flexible member 56 into passageway 68, a fluid-tight seal is made. Inner annular groove 70 within flexible member 56 is adapted to receive lateral circumferential protrusion 44 of housing such that housing 4 is correctly positioned within flexible member 56.

Section 2 may be assembled by inserting septum 22 into passageway 14 and then screwing insert 24 into first end portion 8 of housing 4, thereby compressing septum 22 into surface 18 to form a fluid tight seal therewith. Retaining ring 30 is a split ring. Ring 30 may be slid into circumferential groove 36 until ring 30 surrounds and compresses against housing 4 within groove 36. Second end 10 of housing 4 is slid through passageway 68 of flexible member 56 until groove 70 receives and seals against protrusion 44 of housing 4. O-ring 38 is inserted into second groove 40 of housing 4. Threaded end 50 of shank 46 is screwed into second end 10 of housing 4, threadably engaging inner threaded surface 42.

From the outer view of the fluid collecting section 2 as shown in FIG. 1, shank 46 is hidden from view by bulbous section 62 of flexible member 56. Sharpened drilling end 54 of shank 46 does not extend through opening 72 of bulbous section 62 prior to drilling shank 46 into a container wall, since outer lip 74 of bulbous section 62 must compress against the container wall to provide a seal in order to prevent fluid from escaping to the outside, and also to collect wall shavings (kerf) generated during drilling into the container wall. During operation, the user may clamp first end 8 of housing 4 into the chuck of a power drill. The drill is positioned for drilling by pressing lip 74 of bulbous section 62 against the container wall and compressing bulbous section 62 against the wall until drilling end 54 of shank 46 touches the wall. The user then activates the drill causing the chuck to rotate, which causes all of housing 4, shank 46, and flexible member 56 to rotate. Flexible member 56 may continue to rotate for a time even when compressed against the wall. By pushing the apparatus against the wall while drilling end 54 of shank 46 rotates, drilling end 54 shaves away pieces of the wall (kerf) which are confined by bulbous section 62 and moved out of the way due to its rotation, thereby preventing exposure to the user or environment of kerf which may by contaminated by fluid from the container. When drilling end 54 produces a borehole, shank 46 may be advanced into the container. For sufficiently thick walls, threaded surface 52 of shank 46 taps the borehole. As shank 46 advances into the borehole, flexible member 56 also advances toward the container wall until o-ring 38 compresses against the container wall. Drilling is then discontinued to avoid possible damage to the borehole, container wall, and to o-ring 38. First end portion 8 of housing 4 is then removed from the chuck of the power drill, leaving fluid collecting section 2 affixed to the container wall. If the container is filled with fluid, shank 46 will be in contact with the fluid.

Figure 4:
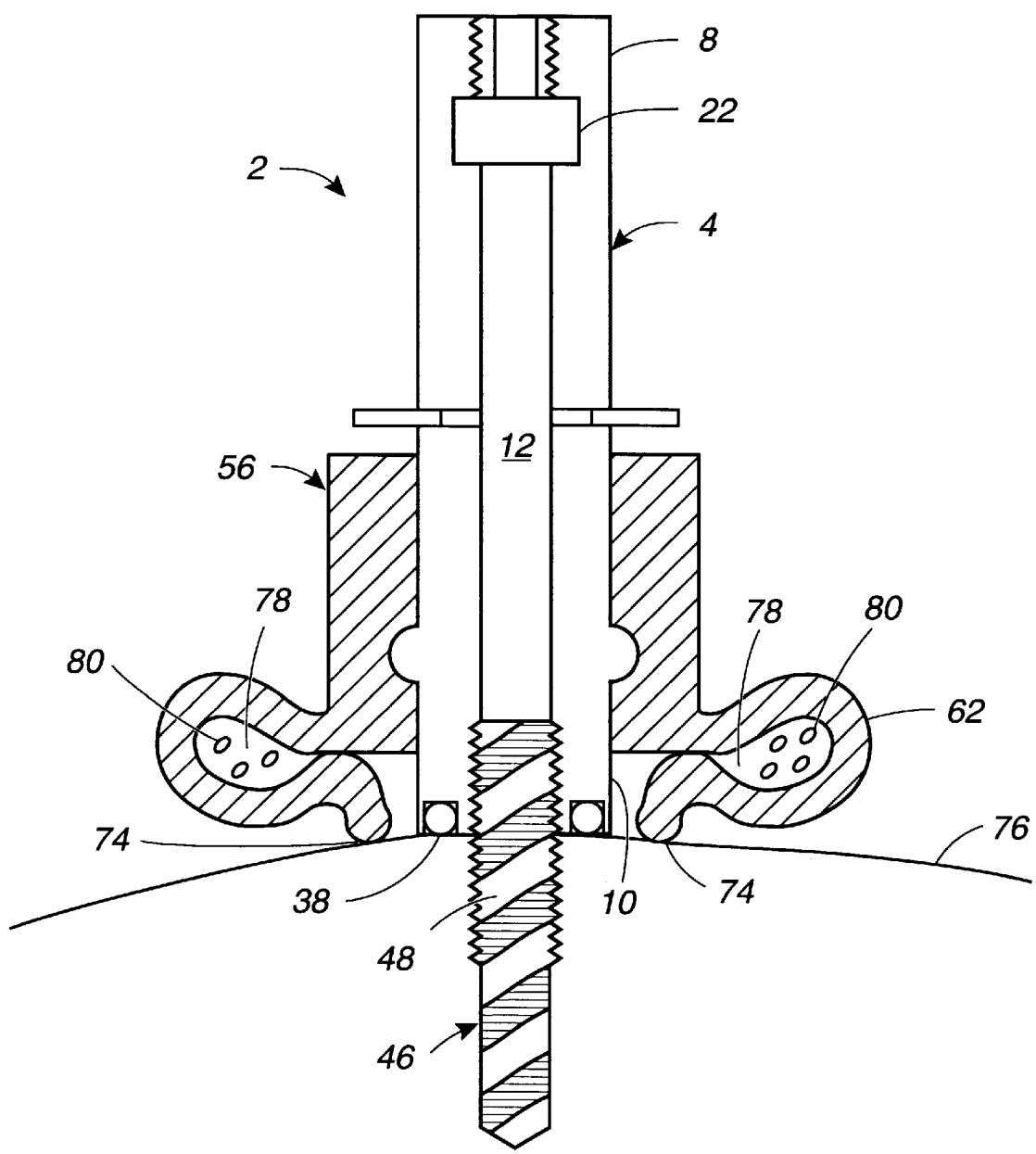
FIG. 4 shows a cross-sectional side view of the the fluid collecting section of FIG. 1 affixed to a container wall.

FIG. 4 shows a cross-sectional side view of fluid collecting section 2 affixed to container wall 76. Bulbous portion 62 is folded and compressed against itself to form chamber 78 in which kerf 80 and fluid are confined. Septum 22 prevents fluid from escaping out of first end 8 of housing 4 while o-ring 38, in sealing engagement with wall 76, prevents fluid from escaping through second end portion 10 of housing 4. If o-ring 38 fails, lip 74 of flexible member 56 provides a seal with wall 76 to provide containment of fluid.

Fluid from within the container may travel along flutes 48 of shank 46 into passageway 12 within housing 4. However, prior to affixing fluid collecting section 2 to container wall 76, passageway 12 is filled with gas (typically atmospheric air) which exerts gas pressure against fluid inside the container. While shank 46 is drilled into wall 76, fluid from within the container fills flutes 48 of shank 46. Fluid may not be able to advance from flutes 48 into passageway 12 if gas pressure exerted by gas in passageway 12 on fluid in flutes 48 exceeds fluid pressure exerted by fluid in flutes 48 on gas in passageway 12. Gas pressure may be reduced by removing at least some of this gas. This can be achieved by passing a hollow needle through septum 22 and allowing gas to vent through the needle. As gas exits passageway 12, it is displaced by fluid from the container. A hypodermic syringe may also be used to remove gas from passageway 12. After a substantial amount of gas has been removed from passageway 12, fluid which has replaced the gas in passageway 12 may be withdrawn by the syringe. When the hypodermic syringe is withdrawn from septum 22, the septum self-seals to prevent leakage of fluid.

Figure 5:
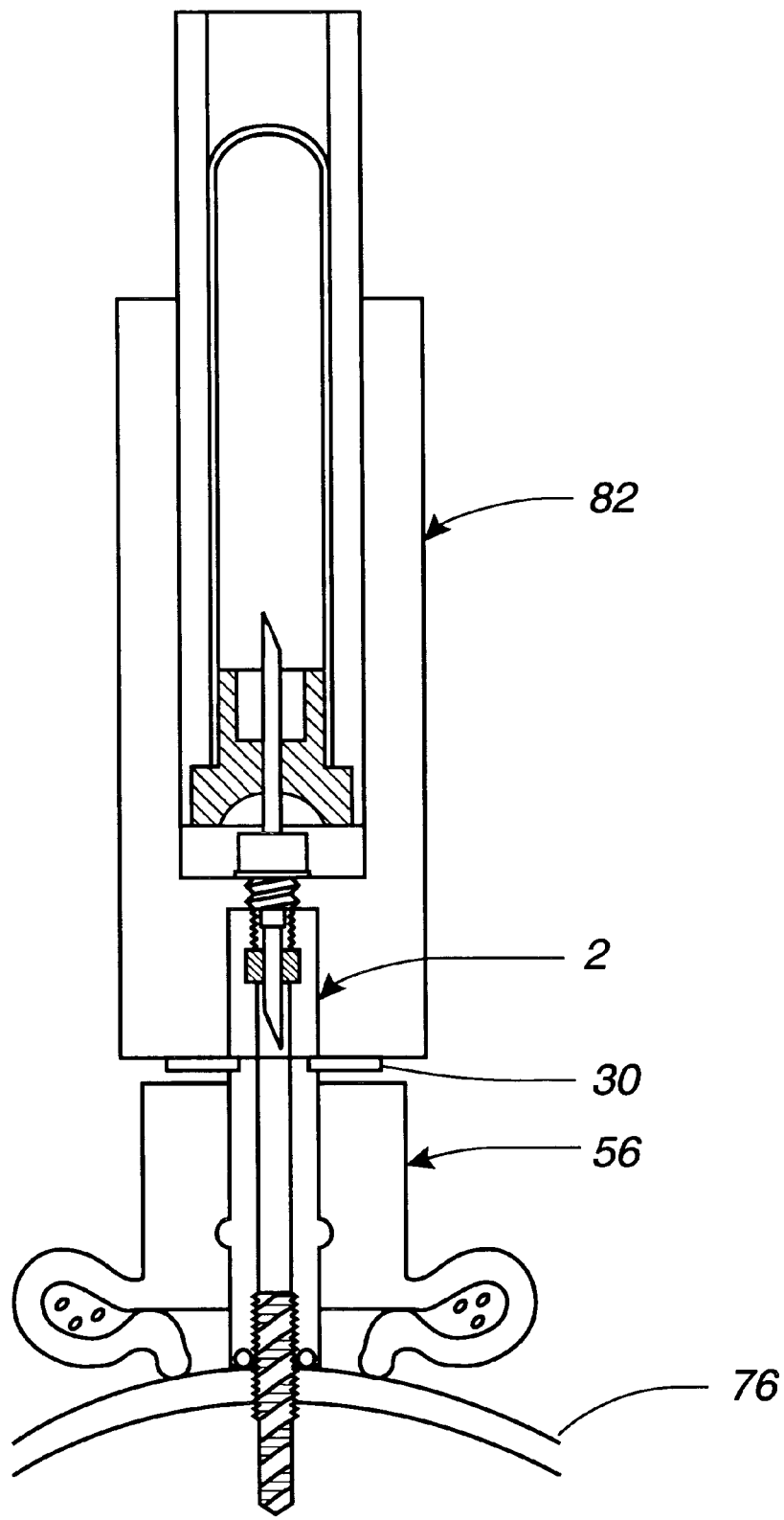
FIG. 5 shows the the fluid extracting section of the present invention engaged to the affixed fluid collecting section of FIG. 4.
Figure 6:
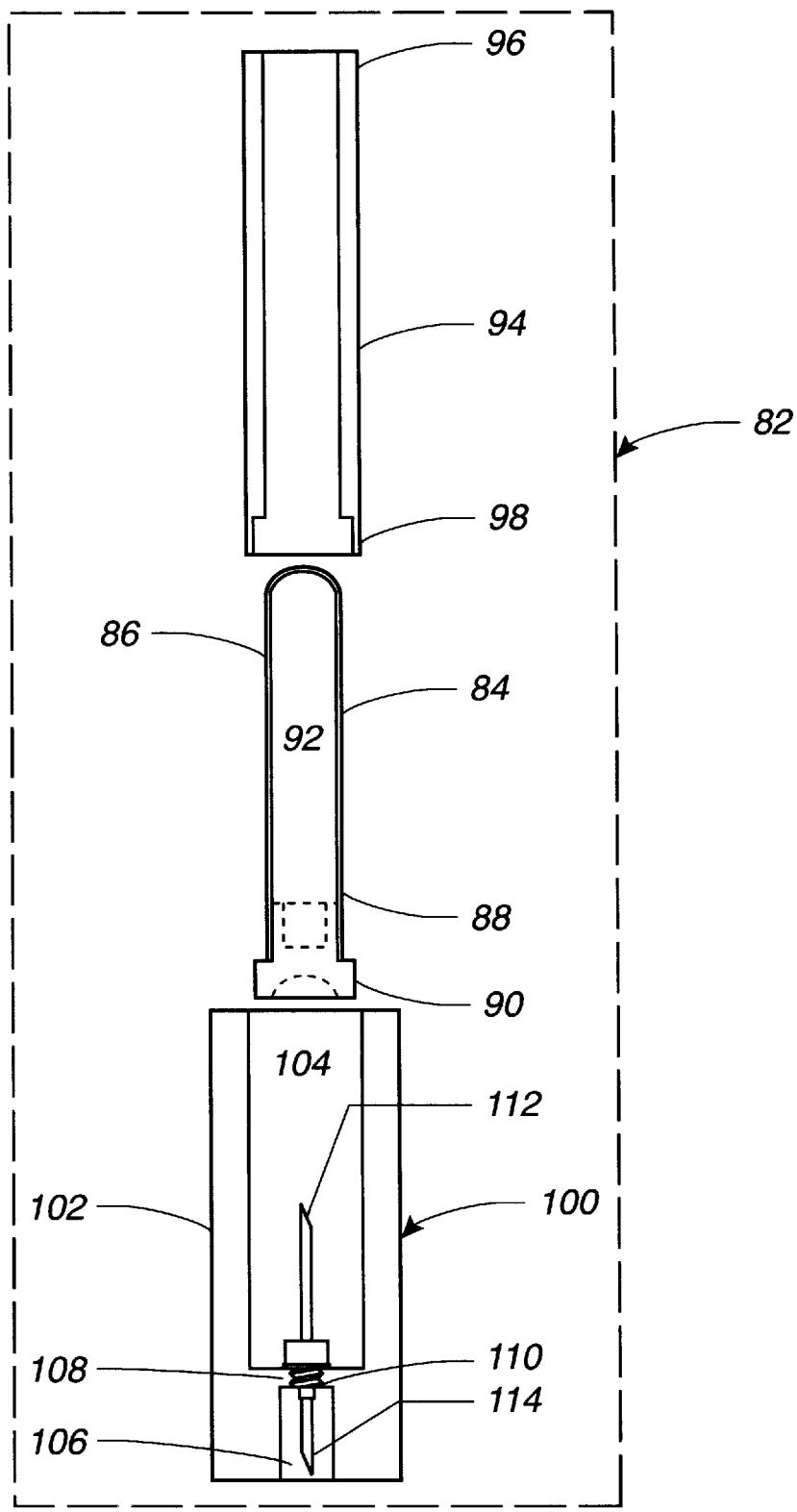
FIG. 6 shows an exploded cross-sectional side view of the fluid extracting section of FIG. 5.

Although a hypodermic syringe may provide adequate means for withdrawing a fluid sample from fluid collecting section 2, other means may be more desirable. FIG. 5 shows fluid collecting section 2 affixed to container wall 76, and fluid extracting section 82 engaged with fluid collecting section 2 during extraction of fluid from collecting section 2, and FIG. 6 shows an exploded view of section 82. Fluid extracting section 82 includes a sample container 84 having a tubular body 86 with an open end 88 which is sealed with a flexible, pierceable plug 90 to provide a chamber 92 which is evacuated prior to sampling. Fluid extracting section 82 also includes tubular sample container housing 94 having a first open end 96 and a second open end 98 configured to receive plug 90 when container 84 is completely within housing 94. Housing 94 provides the user with protection from exposure to container fluid and glass pieces if container 84 is made of glass and damaged during sampling. Fluid extracting section 82 also includes piercing assembly 100 having a tubular body 102 made of a non-fragile material such as polycarbonate or polystyrene plastic and configured to form a pair of volumes 104 and 106 separated by a partition 108 but in fluid communication through a connecting passageway 110 in partition 108. Sample container 84, housing 94, and tubular body 102 may be made out of a transparent material such as polycarbonate or polystyrene in order to enable the user to observe fluid enter sample container 84. Volume 104 is configured to receive housing 94 of sample container 84. Volume 106 is configured to receive housing 4 of fluid collecting section 2. A pair of coaxial hollow piercing members 112 and 114 are attached to partition 108 such that fluid communication between volumes 104 and 106 is maintained. The piercing end of each piercing member points away from the partition. The hollow piercing members may be hypodermic needles and are in leakproof engagement with partition 108.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A rotatable tool for collecting and sampling fluid through a container wall, comprising;
    (a) a drilling member having a fluted shank with a cylindrical threaded tapping section and a drilling end portion for drilling a hole into the wall of the container, whereby kerf is generated,
    (b) a cylindrical housing member having a first end portion, a second end portion, an axis, and an inner axial passageway therethrough, said passageway widening at said first end portion to provide an annular flat surface perpendicular to the housing member axis, the first end portion of said housing member further having a threaded inner surface, the second end portion of said housing member having a threaded inner surface for receiving the threaded shank of said fluted drilling member,
    (c) a septum configured to fit into said widened passageway of the first end portion of said housing member and provide a leakproof seal with said annular surface in the first end portion,
    (d) a cylindrical threaded insert having an axis and an inner axial passageway therethrough, said insert capable of threaded engagement with the widened threaded passageway in the first end portion of said housing and capable of compressing said septum against the annular surface in the first end portion to provide a leakproof seal with the annular surface, and
    (e) a flexible member adapted to form a seal with said housing member, said flexible member also being capable of forming a chamber to enclose kerf generated, said flexible member also being capable of forming a seal with a container wall.

2. The tool as described in claim 1, further including a retaining ring attached to said housing in between said first end portion and said second end portion of said housing for preventing said flexible member from sliding toward said first end portion of said housing member.

3. The tool as described in claim 1, further including a piercing sampling means for withdrawing fluid from said passageway in said housing.

4. The tool as described in claim 1, wherein said flexible sealing member has an axis, a cylindrical portion, and a bulbous portion, the cylindrical portion having a first end and a second end and an inner axial passageway therethrough, the passageway having a diameter such that said housing member may slide though the passageway and form a fluid-tight seal therewith, the bulbous portion being capable of folding to provide a volume for confining kerf, the bulbous portion further having an outer lip capable of providing a seal with the container wall.

5. The tool as described in claim 3, wherein said piercing sampling means comprises a hypodermic syringe.

6. The tool as described in claim 3, wherein the piercing sampling means comprises:

(a) an evacuated container having an open end and a pierceable resealable plug sealingly engaged with the open end of said container, and (b) fluid transferring means having a first piercing end and a second piercing end and a channel therebetween, said fluid transferring means being capable of piercing said pierceable plug of said evacuated container with the first piercing end, and piercing said septum of the first portion of said housing member with the second piercing end, whereby fluid within the passageway of said housing member moves out of the passageway, through the channel, and into said evacuated container.

7. The tool as described in claim 6, wherein said fluid transferring means includes a canula having two pointed ends.

8. The tool as described in claim 6, wherein said fluid transferring means comprises a support, two hypodermic needles coaxially attached to said support, said two needles in fluid tight engagement with the support, said support having a passageway to provide fluid communication between said two needles such that when one of said needles pierces said septum within said housing member and the other of said needles pierces said plug of said evacuated container, fluid may flow from the passageway in said housing member, through the hypodermic needles, and into said evacuated container.

9. The tool described in claim 8, wherein said evacuated container is a tubular container.

10. The tool as described in claim 9, further including a protective tubular housing for said tubular container.

11. The tool as described in claim 10 further including a tubular body attached to said support of said fluid transferring means to provide a first volume and a second volume, the first volume being in fluid communication with the second volume, the first volume being capable of receiving said protective tubular housing, and the second volume being capable of receiving said first end portion of said cylindrical housing member.

12. The tool as described in claim 9, wherein said evacuated container is transparent.

13. The tool as described in claim 10, wherein said is protective housing for said tubular container is transparent.

14. The tool as described in claim 11, wherein said tubular body of said fluid transferring means is transparent.

* * * * *